US007298819B2

United States Patent
Dooley et al.

(10) Patent No.: US 7,298,819 B2
(45) Date of Patent: Nov. 20, 2007

(54) FLEXIBLE TREATMENT PLANNING

(75) Inventors: John R. Dooley, Milpitas, CA (US); Jin-Wu J. Wang, Palo Alto, CA (US); Radhika Mohan Bodduluri, Palo Atlo, CA (US); Jay B. West, Mountain View, CA (US)

(73) Assignee: Accuray Incorporated, Sunnyvale, CA (US)

( * ) Notice: Subject to any disclaimer, the term of this patent is extended or adjusted under 35 U.S.C. 154(b) by 0 days.

(21) Appl. No.: 11/241,658

(22) Filed: Sep. 29, 2005

(65) Prior Publication Data

US 2006/0067469 A1 Mar. 30, 2006

Related U.S. Application Data

(60) Provisional application No. 60/614,574, filed on Sep. 30, 2004.

(51) Int. Cl.
*A61N 5/10* (2006.01)
(52) U.S. Cl. .......................... 378/65; 600/407
(58) Field of Classification Search ............... 378/65; 600/407
See application file for complete search history.

(56) References Cited

U.S. PATENT DOCUMENTS

2002/0051513 A1* 5/2002 Pugachev et al. ............. 378/65
2006/0293583 A1* 12/2006 Saracen et al. ............. 600/407

OTHER PUBLICATIONS

Leksell, L., "The stereotactic method and radiosurgery of the brain", Acta Chirurgica Scandanavica 102 (1951), pp. 316-319.
Holder, A., "A tutorial on radiation oncology and optimization", In Greenberg, H.J., ed.: Tutorials on Emerging Methodologies and Applications in Operations Research. Kluwer Academic Press (2004).
Ferris, M., Lim, J., Shepard, D.: "An optimization approach for the radiosurgery treatment planning", SIAM Journal on Optimization 13 (2003), pp. 921-937.
Cheek, S., Holder, A., Fuss, M. Salter, B.: "The relationship between the number of shots and the quality of Gamma Knife Radiosurgeries." Technical Report 84, Department of Mathematics, Trinity University, San Antonio, TX (2004).
Rosen, I., Lane, R., Morrill, S., Belli, J.: "Treatment plan optimization using linear programming", Medical Physics 18 (1991), pp. 141-152.
Shepard, D., Ferris, M., Olivera, G., Mackie, T.: "Optimizing the delivery of radiation therapy to cancer patients", SIAM Review 41 (1999) pp. 721-744.
Bartolozzi, F., De Gaetano, A., DiLena, E., Marino, S., Nieddu, L., Patrizi, G.: "Operational research techniques in medical treatment and diagnosis: a review." European Journal of Operations Research 121 (2000) pp. 435-466.
Holder, A.: "Radiotherapy treatment design and linear programming". Technical Report 70, Department of Mathematics, Trinity University, San Antonio, TX (2002).

(Continued)

*Primary Examiner*—Courtney Thomas
(74) *Attorney, Agent, or Firm*—Blakely, Sokoloff, Taylor & Zafman LLP

(57) ABSTRACT

A flexible treatment planning system configured to enable the user to utilize both forward planning and inverse planning techniques is described.

41 Claims, 12 Drawing Sheets

OTHER PUBLICATIONS

Dantzig, G.B., Orden, A., Wolfe, P.: "The generalized Simplex method for minimizing a linear form under linear inequality restraints". Pacific Journal of Mathematics 5 (1955), pp. 183-195.

Paddick, I.: "A simple scoring ratio to index the conformality of radiosurgical treatment plans", Journal of Neurosurgery 93 (2000), pp. 219-222.

D. Bechmann, N. Dubreuil, "Animation through space and time base don a space deformation model", The Journal of Visualization and Computer Animation, 4(3) 165-184, 1993.

M. Levoy, et al., "Volume Rendering in Radiation Treatment Planning", Proc. First Conference on Visualization in Biomedical Computing, IEEE Computer Society Press, Atlanta, Georgia, May 1990, pp. 4-10.

PCT International Preliminary Report on Patentability (Chapter I of the Patent Cooperation Treaty), PCT/US2005/035371 filed Sep. 30, 2005, mailed Apr. 12, 2007.

International PCT Search Report and Written Opinion, PCT/US05//35371, Int'l. filing date Sep. 30, 2005, mailing date Nov. 9, 2006, 9 pages.

* cited by examiner

FLEXIBLE TREATMENT PLANNING

RELATED APPLICATION

This application claims the benefit of U.S. Provisional Application 60/614,574, filed Sep. 30, 2004, the contents of which are hereby incorporated by reference herein.

TECHNICAL FIELD

Embodiments of the present invention relate generally to radiation treatment and, more particularly, to treatment planning in radiation treatment.

BACKGROUND

Tumors and lesions are types of pathological anatomies characterized by abnormal growth of tissue resulting from the uncontrolled, progressive multiplication of cells, while serving no physiological function.

Pathological anatomies can be treated with an invasive procedure, such as surgery, but can be harmful and full of risks for the patient. A non-invasive method to treat a pathological anatomy (e.g., tumor, legion, vascular malformation, nerve disorder, etc.) is external beam radiation therapy. In one type of external beam radiation therapy, an external radiation source is used to direct a sequence of x-ray beams at a tumor site from multiple angles, with the patient positioned so the tumor is at the center of rotation (isocenter) of the beam. As the angle of the radiation source changes, every beam passes through the tumor site, but passes through a different area of healthy tissue on its way to the tumor. As a result, the cumulative radiation dose at the tumor is high and the average radiation dose to healthy tissue is low.

The term "radiotherapy" refers to a radiation treatment procedure in which radiation is applied to a target region for therapeutic, rather than necrotic, purposes. The amount of radiation utilized in radiotherapy treatment sessions is typically about an order of magnitude smaller, as compared to the amount used in a radiosurgery session. Radiotherapy is typically characterized by a low dose per treatment (e.g., 100-200 centiGray (cGy)), short treatment times (e.g., 10 to 30 minutes per treatment) and conventional or hyperfractionation (e.g., 30 to 45 days of treatment). For convenience, the term "radiation treatment" is used herein to mean radiosurgery and/or radiotherapy unless otherwise noted by the magnitude of the radiation.

In order to deliver a requisite dose to a targeted region, whilst minimizing exposure to healthy tissue and avoiding sensitive critical structures, a suitable treatment planning system is required. Treatment plans specify quantities such as the directions and intensities of the applied radiation beams, and the durations of the beam exposure. It is desirable that treatment plans be designed in such a way that a specified dose (required for the clinical purpose at hand) be delivered to a tumor, while avoiding an excessive dose to the surrounding healthy tissue and, in particular, to any important nearby organs. Developing an appropriate treatment planning system is especially challenging for tumors that are larger, have irregular shapes, or are close to a sensitive or critical structure.

A treatment plan may typically be generated from input parameters such as beam positions, beam orientations, beam shapes, beam intensities, and radiation dose distributions (that are deemed necessary by the radiologist in order to achieve a particular clinical goal). Sophisticated treatment plans may be developed using advanced modeling techniques, and state-of-the-art optimization algorithms.

Two kinds of treatment planning procedures are known: forward planning and inverse planning. In early days, treatment planning systems tended to focus on forward planning techniques. In forward treatment planning, a medical physicist determines the radiation dose of a chosen beam and then calculates how much radiation will be absorbed by the tumor, critical structures (i.e., vital organs) and other healthy tissue. There is no independent control of the dose levels to the tumor and other structures for a given number of beams, because the radiation absorption in a volume of tissue is determined by the properties of the tissue and the distance of each point in the volume to the origin of the beam and the beam axis. More specifically, the medical physicist may "guess" or assign, based on his experience, values to various treatment parameters such as beam positions and beam intensities. The treatment planning system then calculates the resulting dose distribution. After reviewing the resulting dose distribution, the medical physicist may adjust the values of the treatment parameters. The system re-calculates a new resulting dose distribution. This process may be repeated, until the medical physicist is satisfied by the resulting dose distribution, as compared to his desired distribution. Forward planning tends to rely on the user's ability to iterate through various selections of beam directions and dose weights, and to properly evaluate the resulting dose distributions. The more experienced the user, the more likely a satisfactory dose distribution is produced.

In inverse planning, in contrast to forward planning, the medical physicist specifies the minimum dose to the tumor and the maximum dose to other healthy tissues independently, and the treatment planning module then selects the direction, distance, and total number and intensity of the beams in order to achieve the specified dose conditions. Given a desired dose distribution specified and input by the user (e.g., the minimum and maximum doses), the inverse planning module selects and optimizes dose weights and/or beam directions, i.e. select an optimum set of beams that results in such a distribution.

Inverse planning may have the advantage of being able to produce better plans, when used by less sophisticated users. However, conventional treatment planning systems do not allow a user the flexibility to use both forward planning and inverse planning techniques within a same plan, or to switch back and forth between forward planning and inverse planning. Also, conventional treatment planning systems do not allow a user to incorporate direct modification of the topological map for the isodose distribution. These conventional inverse planning systems may require user definition of anatomical regions to affect the dose distribution. These drawn regions may usually cover a limited percentage of the patient anatomy, and may not fully reflect the clinical goals of the treatment plan. Further, existing treatment planning systems may be based solely on either an isocentric beam geometry or a non-isocentric boundary-targeting beam geometry.

BRIEF DESCRIPTION OF THE DRAWINGS

The present invention is illustrated by way of example, and not by way of limitation, in the figures of the accompanying drawings.

DETAILED DESCRIPTION

Figure 1:
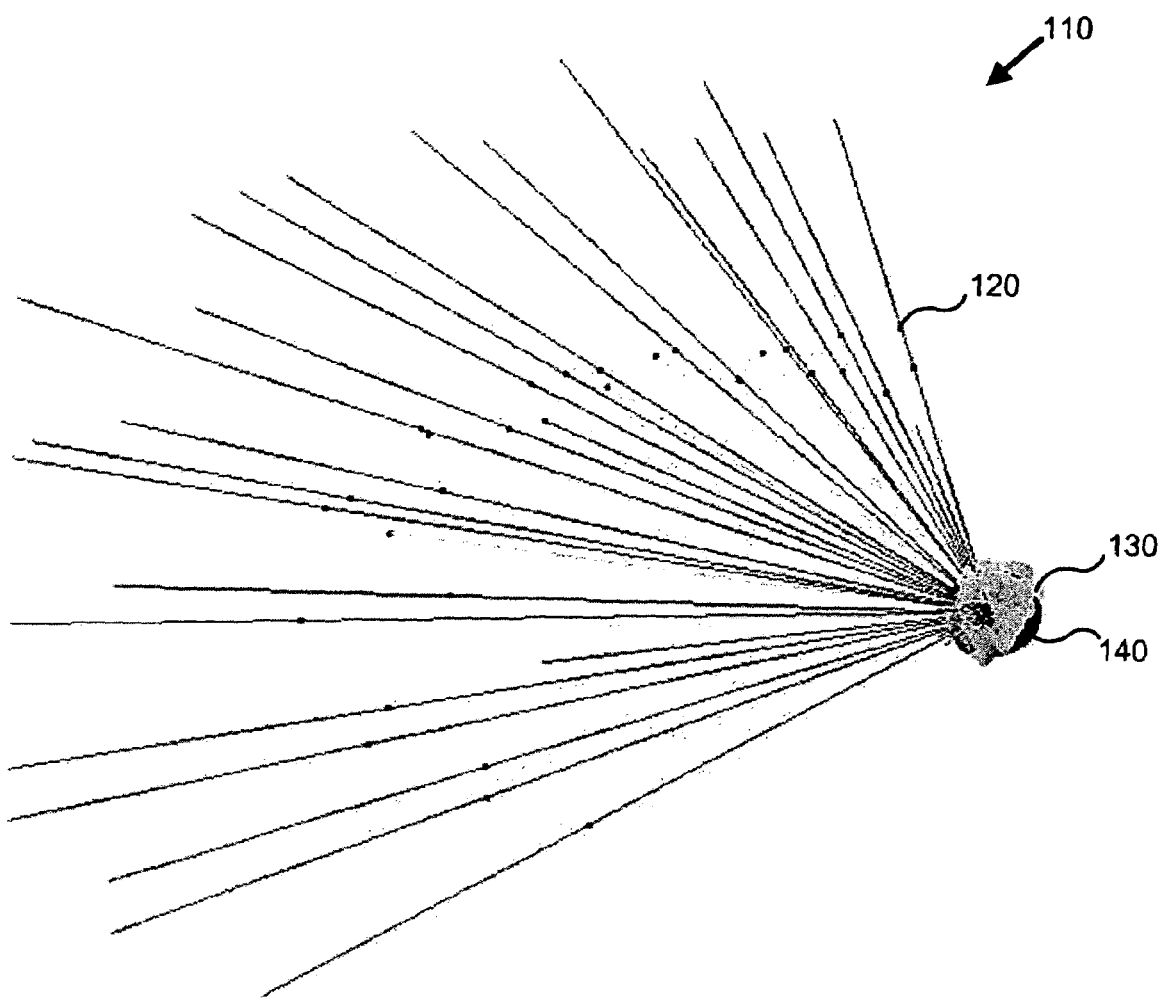
FIG. 1 illustrates an exemplary embodiment of an isocentric beam profile.

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. The term "coupled" as used herein, may mean directly coupled or indirectly coupled through one or more intervening components or systems.

Embodiments of the present invention include various steps, which will be described below. The steps of the present invention may be performed by hardware components or may be embodied in machine-executable instructions, which may be used to cause a general-purpose or special-purpose processor programmed with the instructions to perform the steps. Alternatively, the steps may be performed by a combination of hardware and software.

The treatment planning module and system discussed herein may be implemented using hardware, software, firmware or combinations thereof. For example, a forward planning module that may be composed of hardware, firmware, software, or any combination thereof, may be used to implement the forward planning techniques described herein; an inverse planning module that may be composed of hardware, firmware, software, or any combination thereof, may be used to implement the inverse planning techniques described herein. A forward and inverse planning module (or combination of the separate modules mentioned above) that may be composed of hardware, firmware, software, or any combination thereof, may be used to implement the mixed, or flexible, planning techniques described herein, wherein at least a portion of the treatment plan is developed using forwarding planning techniques and at least another portion of the treatment plan is developed using inverse planning techniques.

The software modules discussed herein may be written in a variety of programming languages, such as, for example, C/C++ and/or Assembly, etc. The operating system (OS) on which the software runs may be a Windows® OS from Microsoft Corporation of Washington or a Mac OS from Apple Computer of California. Alternatively, the OS may be a Unix, Linux, or other operating systems (e.g., embedded or real-time operating system), etc. The software and OS may be run on any type of platform, for example, a personal computer (PC) platform, workstation, etc.

A software module, or computer program product, may include a machine-readable medium having stored thereon instructions, which may be used to program a computer system (or other electronic devices) to perform a process. A machine-readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; electrical, optical, acoustical, or other form of propagated signal (e.g., carrier waves, infrared signals, digital signals, etc.); or other type of medium suitable for storing electronic instructions.

Unless stated otherwise as apparent from the following discussion, it will be appreciated that terms such as "processing," "selecting," "determining," "generating," "weighting" or the like may refer to the actions and processes of a computer system, or similar electronic computing device, that manipulates and transforms data represented as physical (e.g., electronic) quantities within the computer system's registers and memories into other data similarly represented as physical within the computer system memories or registers or other such information storage, transmission or display devices. Embodiments of the method described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

Some portions of the description that follow are presented in terms of algorithms and symbolic representations of operations on data bits that may be stored within a memory and operated on by a processor. These algorithmic descriptions and representations are the means used by those skilled in the art to effectively convey their work. An algorithm is generally conceived to be a self-consistent sequence of acts leading to a desired result. The acts are those requiring manipulation of quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, parameters, or the like.

A flexible treatment planning module (FTPM) for radiosurgery is described. In one embodiment, a hybrid approach to treatment planning may be used that integrates both forward and inverse planning techniques (e.g., isocentric and non-isocentric beam geometries) to develop a treatment plan and, thereby, allows a user to engage in both forward and inverse planning modes during treatment planning. In one embodiment, the user can produce a plan using a partial set of beams generated using one or more forward planning approaches and the rest of the beams by one or more inverse planning approaches. In another embodiment, the user can produce a plan generated by forward planning technique with a set of beams and initiate an inverse planning scheme to improve the plan. In another embodiment, the user can produce a plan generated by inverse planning technique with a set of beams and initiate forward planning scheme to improve the plan. In another embodiment, the user can produce a plan generated by either forward or inverse planning technique and enhance the plan by either inverse or forward planning technique with additional beams, respectively. In another embodiment, the user can produce a plan generated by forward planning approach by adjusting beam weights based on a selection of one or more beams. In another embodiment, the user can produce a plan generated by inverse planning approach by using only beams selected based on one or more specific characteristics of the beams. These embodiments are described in more detail below.

Although a specific type of target such as a pathological anatomy (such as a tumor, legion, arteriovenous malformation, etc.) may be referred to below for ease of explanation purposes, the method and apparatus described herein may be applied to other types of targets (e.g., non-biological) and other types of objects (non-human).

In forward planning, a user (e.g., medical physicist) chooses the directions of the beams and the intensity of the beams and then the treatment planning module calculates and displays the resulting dose distribution. More specifically, the user may specify particular directions and intensities for the radiation beams to be generated by the radiation treatment delivery system, choosing from a subset of available beams determined by constraints on the delivery system itself. The user may "guess" or assign, based on his or her experience, values to beam directions and intensities, or weights. The treatment planning system then calculates the resulting dose distribution. By evaluating the dose distribution, the user may manually change his or her selection of beams in an attempt to improve the dose distribution. The feedback given to the user is the dose profile corresponding to the current plan where beams may be removed, changed or added until the dose profile is deemed acceptable. After reviewing the resulting dose distribution, the user may adjust the values of the treatment parameters. The system re-calculates a new resulting dose distribution. This process may be repeated, until the user is satisfied by the resulting dose distribution, as compared to a desired distribution.

FIG. 1 illustrates an exemplary embodiment of an isocentric beam profile. In one embodiment where a forward planning process is used, at least in a part, an isocentric beam profile 110 may be produced. In order to generate such a profile, an external radiation source is used to direct a sequence of x-ray beams (e.g., beam 120) at a tumor target 130 from multiple angles, with the patient being positioned so the tumor is at the center of rotation (isocenter) of the beams. Each available beam is targeted at the same point to form the "isocenter," which generally may be a roughly spherical isodose region as represented by sphere 140. Accordingly, isocentric planning may be often applied when treating a tumor that has a substantially regular (e.g., spherical) shape. As the angle of the radiation source is changed, every beam passes through the tumor, but may pass through a different area of healthy tissue on its way to the tumor. By stacking isocenters within a target volume, a plan may be developed that ensures that nearly all the target receives a sufficient dose. As a result, the cumulative radiation dose at the tumor may be high and the average radiation dose to healthy tissue may be low.

In one embodiment, a linear or non-iterative algorithm that performs convex optimization may be used to perform forward planning, for example a Simplex algorithm. Such an algorithm operates to minimize the number of monitor units (MUs) subject to the minimum/maximum dose constraints. A Simplex algorithm is known in the art; accordingly, a detailed description is not provided. It should be noted that a forward planning process may not necessary be the same as an isocentric planning process.

Figure 2A:
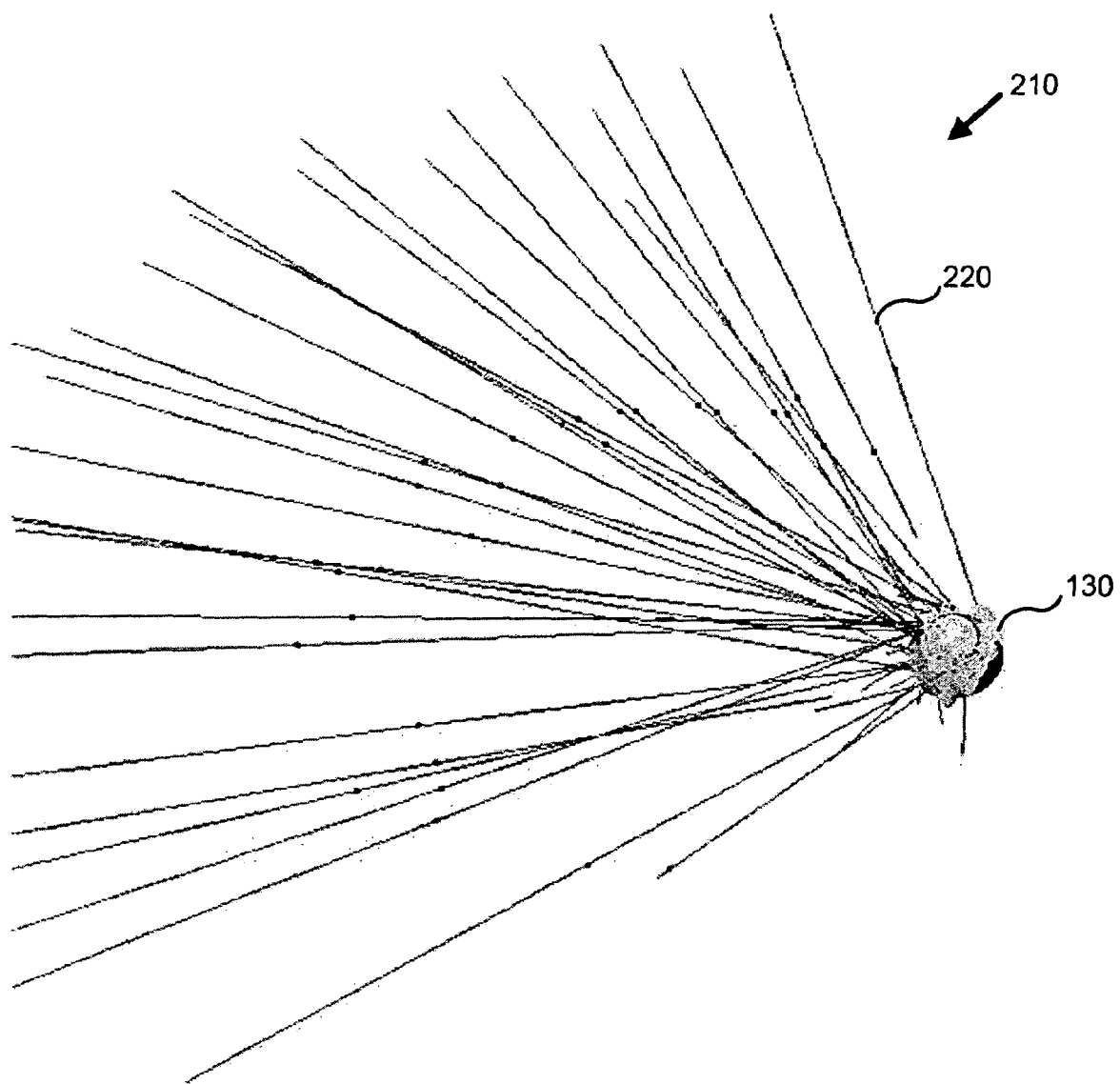
FIG. 2A illustrates an exemplary embodiment of non-isocentric beam profile.

FIG. 2A illustrates an exemplary embodiment of non-isocentric beam profile. In an embodiment where inverse planning process (which may also be referred as conformal planning) is used, at least in part, a non-isocentric beam profile 210 is produced. In inverse treatment planning, some beams may or may not intersect or converge at a common point (the isocenter). Although some of the beams may appear to intersect in the perspective of FIG. 2A, the beams may not intersect in their actual three-dimensional space. The radiation beams (e.g., beam 220) need only intersect with the target 130 and do not necessarily converge on a single point, or isocenter, within the target 130.

Figure 2B:
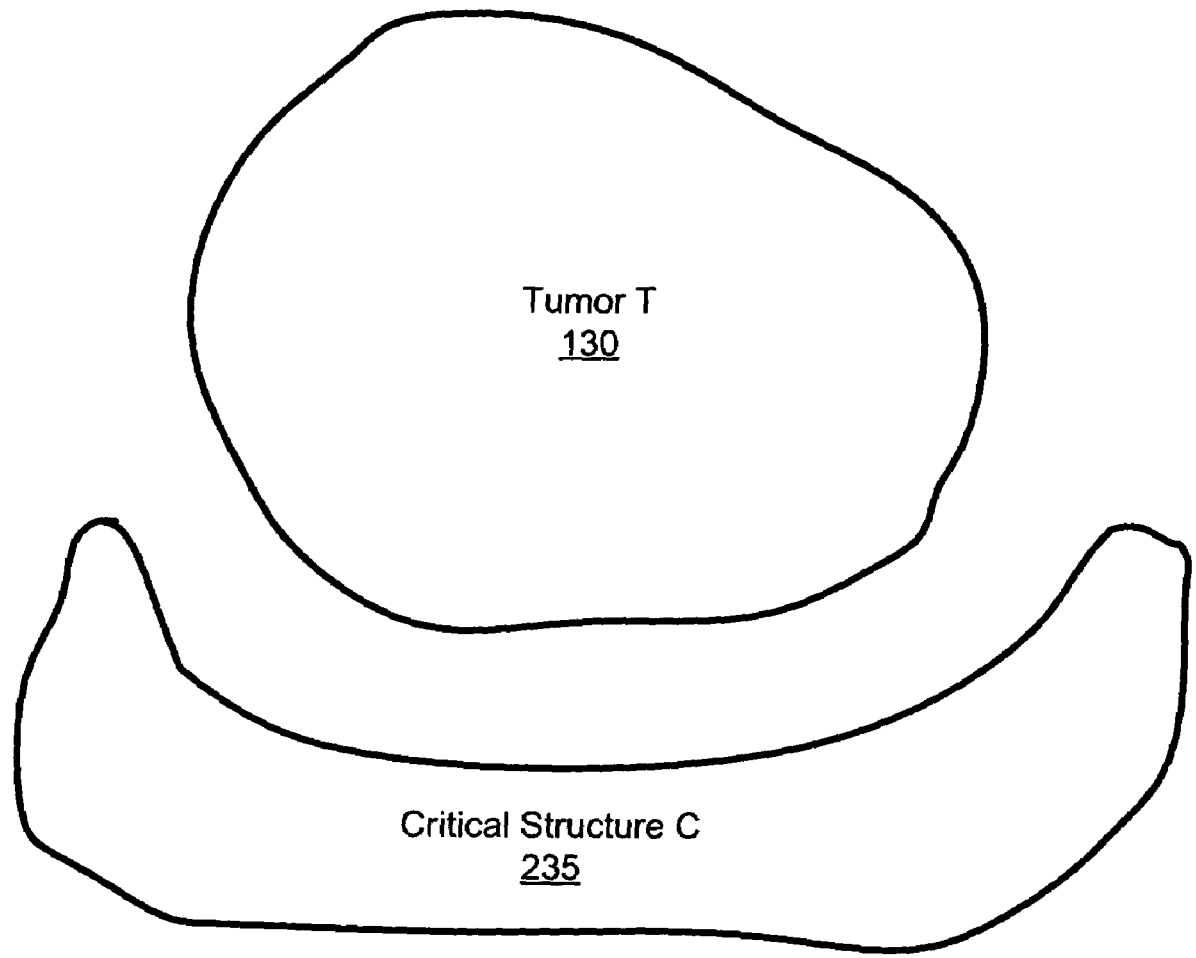
FIG. 2B illustrates one embodiment of a tumor T and critical structure C delineated.

In one embodiment, an inverse planning process may generally proceed as follows. Find a plan so that an objective function J is minimized while meeting the constraints on doses in tumor(s) and other critical structures. Given a tumor region T and a critical region C, as shown in FIG. 2B, the inverse planning problem is formulated as follows:

Find the plan x with beams that minimizes the objective function J(x) such that $D_T(x) < D_{Tmax}$ for each pixel in Tumor T
$D_T(x) > D_{Tmin}$ for each pixel in Tumor T
$D_C(x) < D_{Cmax}$ for each pixel in Critical structure C.

The objective function J itself is defined in different ways depending on the planning system. The optimization variables x vary also depending on the planning system. In one embodiment, the treatment planning system uses the objective function J as the total monitor units of all the beams. The selection of the linear objective function and the linear formulation of constraints enable optimization using linear programming.

In one embodiment, the inverse-planning process may be well suited for the user (e.g., physician or the physicist) to specify the doses required to kill a tumor and maximum doses allowed in the critical structures. An inverse planning process to specify the dose distributions based on the anatomy region may be referred to as region-based inverse planning. One of the assumptions of the region-based inverse planning is that the objective function is intelligently formulated such that the result of the optimization while meeting the user specified constraint criteria results in an overall optimal dose distribution. An optimal dose distribution, in the most ideal sense, is the uniform dose in Tumor equaling $D_{Tmin}$, and zero everywhere else. While this is not practical, the optimization strives to achieve the best it can, based on the objective function.

In one embodiment, the dose calculation in the inverse planning process considers a set of beams that are directed at the tumor 130. In this embodiment, the inverse planning process is used with a radiation source that has a collimator that defines the width of the set of beams that is produced. For each tumor 130, for example, the number of beams, their sizes (e.g., as established by the collimator), their positions and orientations are determined. Having defined the position, orientation, and size of the beams to be used for planning, how much radiation should be delivered via each beam is also determined. The total amount of radiation exiting the collimator for one beam is defined in terms of Monitor Units (MU). Because the intensity of the radiation source is constant, the MU is linearly related to the amount of time for which the beam is enabled. The radiation dose absorbed (in units of cGy) by tissue in the path of the beam is related to the MU. The absorbed dose related to a beam is also affected by the collimator size of the beam, the amount of material between the collimator and the calculation point, the distance of the collimator from the calculation point, and the distance of the calculation point from the central axis of the beam.

Figure 2C:
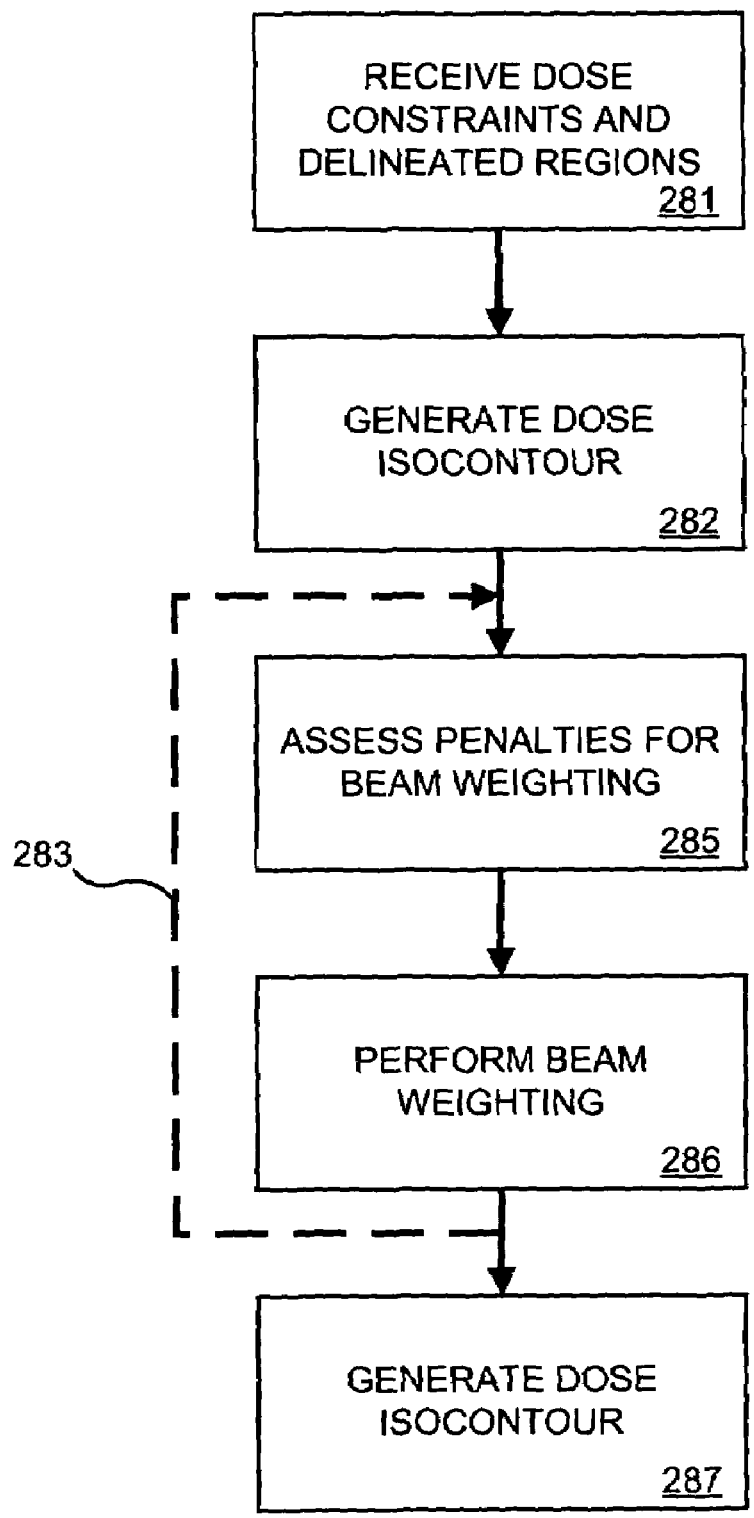
FIG. 2C is a flow chart illustrating one embodiment of an inverse planning method.

FIG. 2C is a flow chart illustrating one embodiment of an inverse planning method. In this embodiment, the inverse planning method utilizes an iterative routine that enables alterations to treatment plan without requiring re-initialization of the optimization process.

In one embodiment, the treatment planning algorithm receives as input from a user, step 281, the delineated target region 130 and any critical region 235 on one or more slices of a CT image; and (2) dose constraints defining the minimum and maximum doses for target region 130 and the maximum dose for the critical region 235. It should be noted that additional dose constraints for additional regions may also be provided. The delineation of the regions and the dose constraints may be performed in any order. In one embodiment, a dose isocontour may be generated by the treatment planning module for a given dose percentage (e.g., 60%, 70%, 80%, etc.) of the maximum dose as displayed to the user, step 282. The generation of a dose isocontour is known in the art; accordingly, a more detailed description is not provided.

In one embodiment, the treatment planning module assesses any penalties that may be assigned, step 285, before performing beam weighting. Whether any penalties should be assessed when performing beam weighting may be based, for example, on the dose constraints for a dose voxel, in order to reduce dose to a given sensitive organ to minimal levels. A beam intersecting such position may be given a penalty such that it is automatically set to have zero MU in the final plan.

Then, beam weighting is performed in step 286. The user or the treatment planning module assigns an arbitrary weighting to each of one or more beams of the radiation treatment system. This weighting may be determined using an algorithm designed to give a suitable "start point" for planning, may be randomly chosen, or may simply be a constant weighting for each beam.

Then, the treatment planning algorithm performs beam weighting of each one or more beams of the radiation treatment system to be used in the treatment plan according to the inputs provided by the user above. In one particular embodiment, to begin the beam weighting, step 286, an assumption may be made that the size and trajectory of the beam set has been defined. Let the beam set be $\{B_i; 1 \leq i \leq N\}$, where N≈500. Each of the beams illustrate in FIG. 2A has a weight (e.g., a number of MU assigned to the beam, or how long a beam will be maintained on) associated with it. The weight in MU of each beam is designated by $w_i$. The delineated regions are represented as objects $T_j$, with corresponding minimum and maximum allowed dose $min_j$ and $max_j$, and critical structures (critical region 235) $C_j$, with corresponding $max_j$ defined. Each region has an integer priority $p_j \epsilon [0,100]$ defining the relative importance of the dose constraints applied to that region. For each beam, a dose value mask is created. The dose value mask provides a linked list of floating point values and positions $d_i(r)$ where r is the position within the dose calculation volume, and $d_i$ is the dose in cGy delivered to r by beam i when $w_i$ is set to unity. Thus, the total dose at r is given by:

$$D(r) = \sum_{i=1}^{N} w_i d_i(r). \tag{1}$$

For each $B_i$, we define a beam value $v_i$, where $$v_i = \frac{\sum_j \sum_{r \in T_j} r \in T_j d_i(r)}{\sum d_i(r)},$$  (2)

The beam value is the ratio of dose delivered into tumor 130 to total dose delivered. To define the initial set of $w_i$ for optimization, we set $w_i = v_i$, $\forall i$. The maximum dose within the dose calculation volume, $D_{max}$, is computed and the beam weights renormalized so that the new maximum dose is equal to the largest of the maximum dose constraints, $\max_j$. Hence, this provides:

$w_i = v_i \sup(\max_j)/D_{max}.$  (3)

At one iteration of the treatment planning algorithm, the optimization process looks at all of the dose values in the dose volume and determines if the target tumor 130 and critical structure 235 are within the dose constraints.

Given the initial weights, the optimization process then alters the beam weights so that the treatment solution is closer to meeting the provided dose constraints. First, a set of $\Delta w_i$, the amount by which each beam weight may be changed, is defined:

$$\Delta w_i = \Delta^{(0)} w_i = \frac{s}{4N} \sum_{i=1}^{N} w_i, \forall i$$  (4)

where s is the search resolution, having an initial value of 1.

The optimization process iterates through one or more of the beams and for each of the beams, if a beam weight is increased or decreased by a certain amount, determines the resulting dose distribution from such a change (i.e., how such a change alters the amount of violation of the treatment plan constraints). For example, an increase in one or more of the beam weights may typically help in achieving the constraint in the target (e.g., tumor) region but, depending on the location of the beam, it may also hurt in the critical region due to a possible resulting increase of dose above the maximum value in the critical region.

The optimization process traverses the volume of interest, adds up all the penalties that are incurred by the increase in a beam weight, adds up all the penalties that are incurred by the decreasing the beam weight (e.g., under-dosing the target region), and then provides a result. In one embodiment, a multiplier may be used with each penalty to stress the importance of one constraint (e.g., minimum dose value in the target region) versus another constraint (e.g., maximum dose value in the target region). For example, it may be more important to achieve a minimum dose value than to stay under the maximum dose value in the target region.

The optimization process then updates the dose and goes on to the next beam and repeats the process until it has made its way through the beam set. The optimization process then reaches a stage where it has looked at all of the different weights for each of the beams at the different dose levels and selects the beam weight that provides the optimal resulting dose values in both the target region and critical region.

More particularly, in one embodiment, the iterative optimization process proceeds as follows: Iterate over the beams in decreasing order of $v_i$. For each beam $B_j$, calculate $P_j^+$ and $P_j^-$, the relative penalties for respectively increasing or decreasing $w_j$, that are defined as:

$$P_j^+ = \sum_i \frac{p_i}{V_i} \sum_{r \in T_i \cup r \in C_i} \Delta w_j d_j(r) \max\left(0, \min\left(1, \frac{D(r) + \Delta w_j d_j(r) - \max_i}{\Delta w_j d_j(r)}\right)\right) - $$

$$\sum_i \frac{p_i}{V_i} \sum_{r \in T_i} \Delta w_j d_j(r) \max\left(0, \min\left(1, \frac{\min_i - D(r)}{\Delta w_j d_j(r)}\right)\right), \text{ and}$$

$$P_j^- = \sum_i \frac{p_i}{V_i} \sum_{r \in T_i} \Delta w_j d_j(r) \max\left(0, \min\left(\frac{\min_i - D(r) + \Delta w_j d_j(r)}{\Delta w_j d_j(r)}\right)\right) - $$

$$\sum_i \frac{p_i}{V_i} \sum_{r \in T_i \cup r \in C_i} \Delta w_j d_j(r) \max\left(0, \min\left(1, \frac{D(r) - \max_i}{\Delta w_j d_j(r)}\right)\right),$$

where $V_i$ is the volume in mm³ of region i. Hence, the penalty for this beam is the sum of the additional amount of over-dosing and under-dosing that would be created by the change in the beam, weighted by the priorities of the different regions and normalized according to the region volumes. If $P_j^-$ and $P_j^+$ are both positive, $w_j$ is kept the same, otherwise change $w_j = w_j \pm \Delta w_j$ according to whichever of $P_j^-$ and $P_j^+$ i smaller. If the previous iteration moved $w_j$ in the same direction as this iteration, the following is set:

$\Delta w_j = \Delta w_j + \Delta^{(0)} w_j,$  (5)

else set:

$\Delta w_j = \Delta^{(0)} w_j.$  (6)

The change in dose according to $\Delta w_j$ is computed and applied to the dose volume before the optimization process moves on to a next beam, because a correct decision on how to change the beam weight assumes an up-to-date view of the dose including change sin previous $w_i$. If all $w_j$ remained unchanged by the current iteration, s is reduced by a factor of 2. The process may iterate (indicated by the dashed line 283) to generate a more optimized result. In one embodiment, the treatment planning module may generate an optimized dose isocontour that may be displayed to the user, step 287.

The optimization process described above may also provide feedback to the user via an update to the dose isocontours and/or dose volume histograms (DVHs), after each iteration in the optimization process. In one embodiment, beam statistics may also be displayed to the user, for example, the total MU and number of beams, the minimum non-zero MU of all currently existing beams and the maximum MU. These statistics may also be continually updated by the treatment planning module at the end of each optimization iteration. Accordingly, it is easy to make small modifications to the plan without going through the entire solution process. In an alternative embodiment, other iterative and non-linear optimization algorithms may be used.

Figure 3:
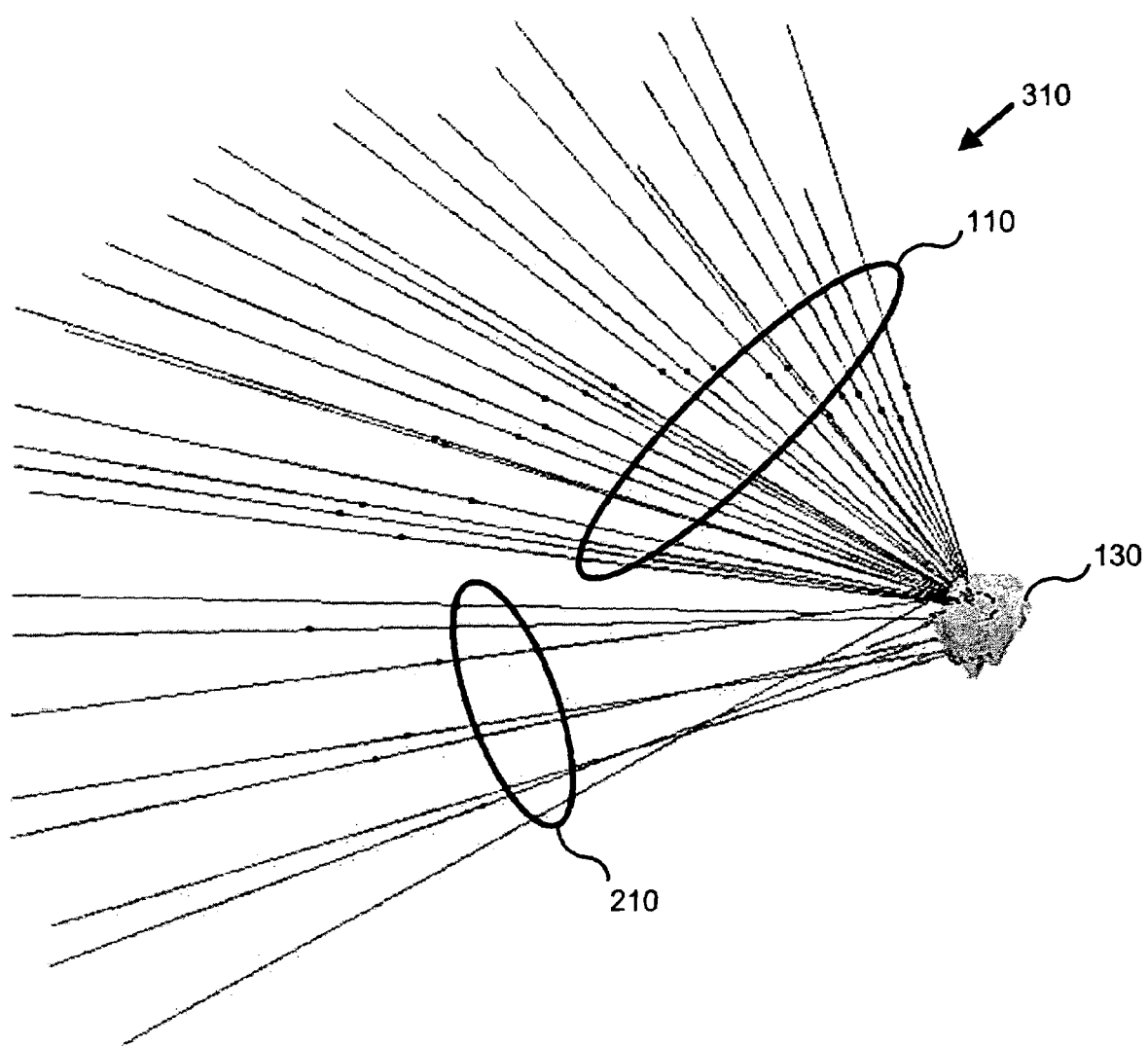
FIG. 3 illustrates an exemplary embodiment of a combined isocentric and non-isocentric beam profile.

FIG. 3 illustrates an exemplary embodiment of a combined isocentric and non-isocentric beam profile. In an embodiment where a combined forward and inverse planning module (referred to as FTPM) is used to generate a combined beam profile 310 composed of an isocentric beam profile 110 and a non-isocentric beam profile 210. The beam profile 110 of the forward planning process may be used, for example, to target an inner volume of the tumor 130, while the beam profile 210 of the inverse planning process may be used, for example, to target the outer periphery of the tumor 130. The combination of the forward and inverse planning process may, thus, permit very complex tumor surfaces and volumes to be accurately irradiated so that a more accurate and complete treatment of the tumor can be performed. It should be noted that number of beams illustrated in FIGS. 1-3 are only for ease of illustration and that an actual treatment plan may include more, or fewer, than the illustrated number of beams.

Each beam in a treatment planning system may be characterized by a radiation emission point, a distance to the tumor target 130, an orientation, and a radiation dose weight. The FTPM enables the user to control these characteristics. FTPM allows the user to specify which beams (e.g., a first subset of the system's beams) should be selected using forward planning, and which beams (e.g., a second subset of system's beams) should be selected using inverse planning. Each beam in the first subset may be characterized by user-generated values representative of radiation emission point, target point, orientation, and radiation dose weight. In other words, each beam in the first subset is generated using forward planning. Each beam in the second subset may be generated using inverse planning. The radiation emission point, target point, orientation, and radiation dose weight for the beams in the second subset are generated by the treatment planning module in such a way that at least a portion of a desired radiation dose distribution profile is achieved.

For instance, the user may produce a plan generated by a forward planning approach, by adjusting beam weights based on a selection of one or more beams. Alternatively, the user can produce a plan generated by the inverse planning approach, by using only beams selected based on one or more specific characteristics of the beams. Alternatively, the user can use a partial set of beams generated using a forward planning approach, and the rest by one or more inverse planning approach.

By way of example, in one embodiment, the user may produce a plan that uses forward planning to create one or more isocenters that distribute the radiation dose to the central part of the target 130 as discussed above. Inverse planning is then used to shape the dose in the proximity of the target 130 boundary (i.e., the outer periphery). The central dose to the tumor 130 is constrained using the sum of the effect of the non-isocentric shaping beams and the constant previously calculated dose from the isocentric forward planning process. Alternatively, the user can first use inverse planning to create a dose distribution around the boundary of target 130. Forward planning is then used to fill the dose in the central portion of the target 130.

In another embodiment, the user may target isocentric beams as in a forward planning process, but not assign dose weightings to those beams. The inverse planning algorithm uses sculpting beams around the boundary of the target 130 and the full weight of the isocentrically targeted beams to generate a dose distribution for treatment of the target 130.

In operation, the user of FTPM determines the tumor location and boundaries, based on pre-operative image (e.g., CT, PET, MRI, etc.). The user then determines beam geometries. For example, the user inputs desired values for the beam diameters, and decides whether the beams should be isocentric or non-isocentric. Next, the user sets the acceptable dose ranges for predetermined regions such as the tumor 130 and the critical structure 235, i.e. the upper and lower limits of radiation for delivering the requisite doses of radiation to the tumor 130, and avoid the critical structure 135. The FTPM finds the optical solution, i.e. the optimal set of beams and associated characteristics (such as beam paths and dose weights) that satisfies these constraints imposed by the user. In one embodiment, a linear optimization algorithm, as described above, may be used to determine the optical dose weights and beam directions.

Figure 5:
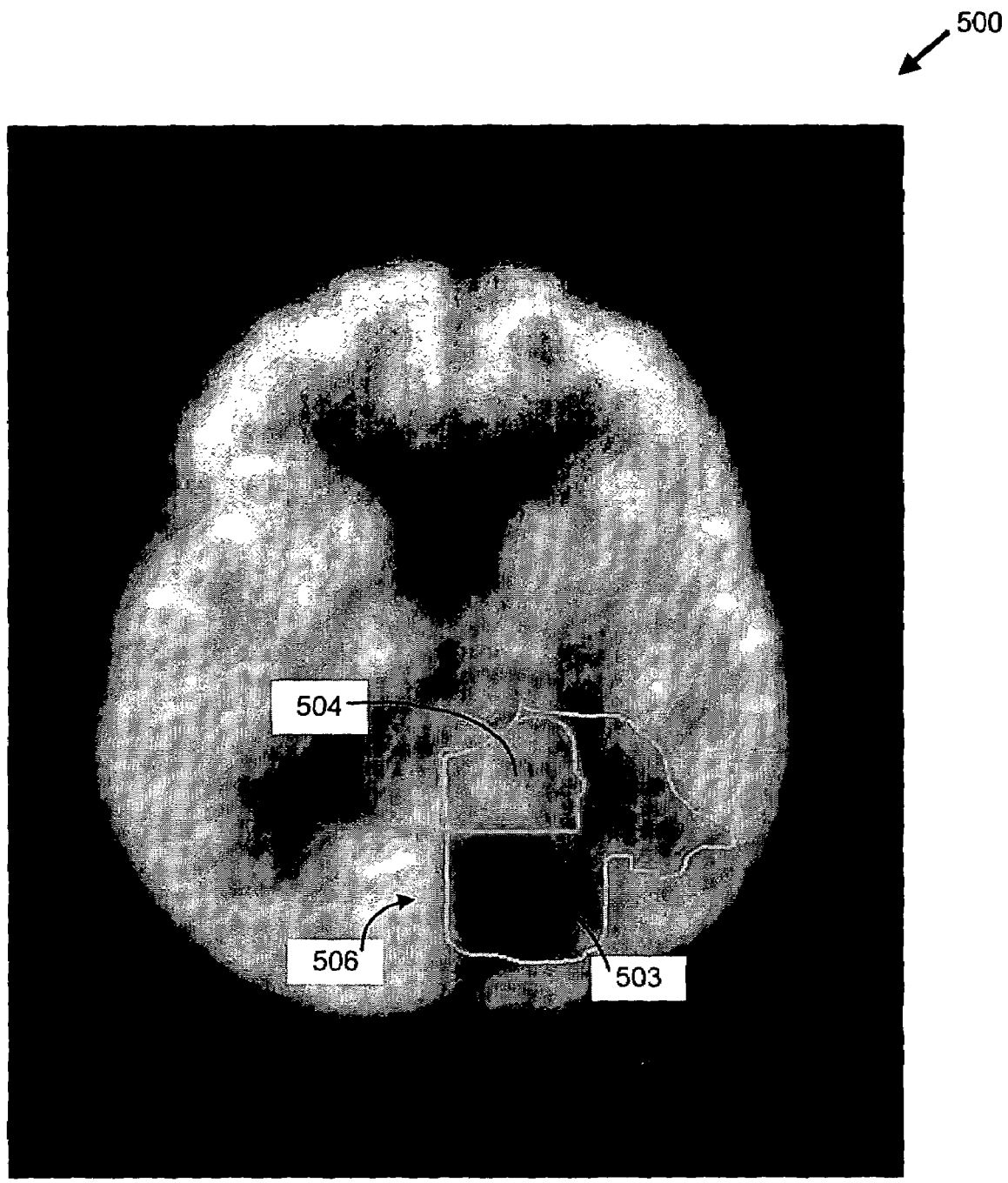
FIG. 5 illustrates a functional PET image 500 of an intra cranial axial view.

It should be noted that the FTPM is not limited to only divisions of forward planning and inverse planning to treat bulk and boundary areas, respectively, of a substantially regular shaped (e.g., spherical) tumor target as was discussed in an exemplary manner above. In another embodiment, both forward and inverse planning techniques may be used to treat the same portions of a tumor, which may be regardless of tumor shape. For example, if a tumor has a region of higher intensity relative to other regions in the tumor (e.g., region 503), inverse planning may be used to treat the entire tumor region and forward planning may be used to treat the higher intensity region. FIG. 5 illustrates a functional PET image 500 of an intra cranial axial view. A lesion, for example, does not necessarily have a uniform distribution of cells within the volume occupied by the lesion. Functional images such as PET scans can provide data relating to the differences in cellular activity within the lesion volume. Fluorodeoxyglucose (FDG), a radioactive sugar molecule, is used to produce images that demonstrate increased glucose metabolism associated with regions of lesion activity. Because cancer cells grow and divide more rapidly than normal cells, they metabolize more sugar for fuel. This increased activity identifies them as cancer in FDG-PET scanning. For this procedure, the patient is injected with the FDG and lies in a PET camera for the imaging. Areas of activity from PET images are also represented by differences in image intensity. Especially beneficial is the data shown with respect to tissue activity for lesion 506, which shows a higher intensity region 504, indicating an area of high glucose metabolism, and therefore higher lesion cell content. Accordingly, inverse planning may be used to treat the entire tumor region 506 and forward planning may be used to treat the higher intensity region 504.

In alternative embodiments, the inverse planning techniques, or a combination of the inverse and forward planning techniques of the FTPM, may also be used to treat other target shapes and regions, for examples, ring shaped, crescent, elongated, etc. by selecting only certain beams based on various geometric and physical characteristics.

Figure 6:
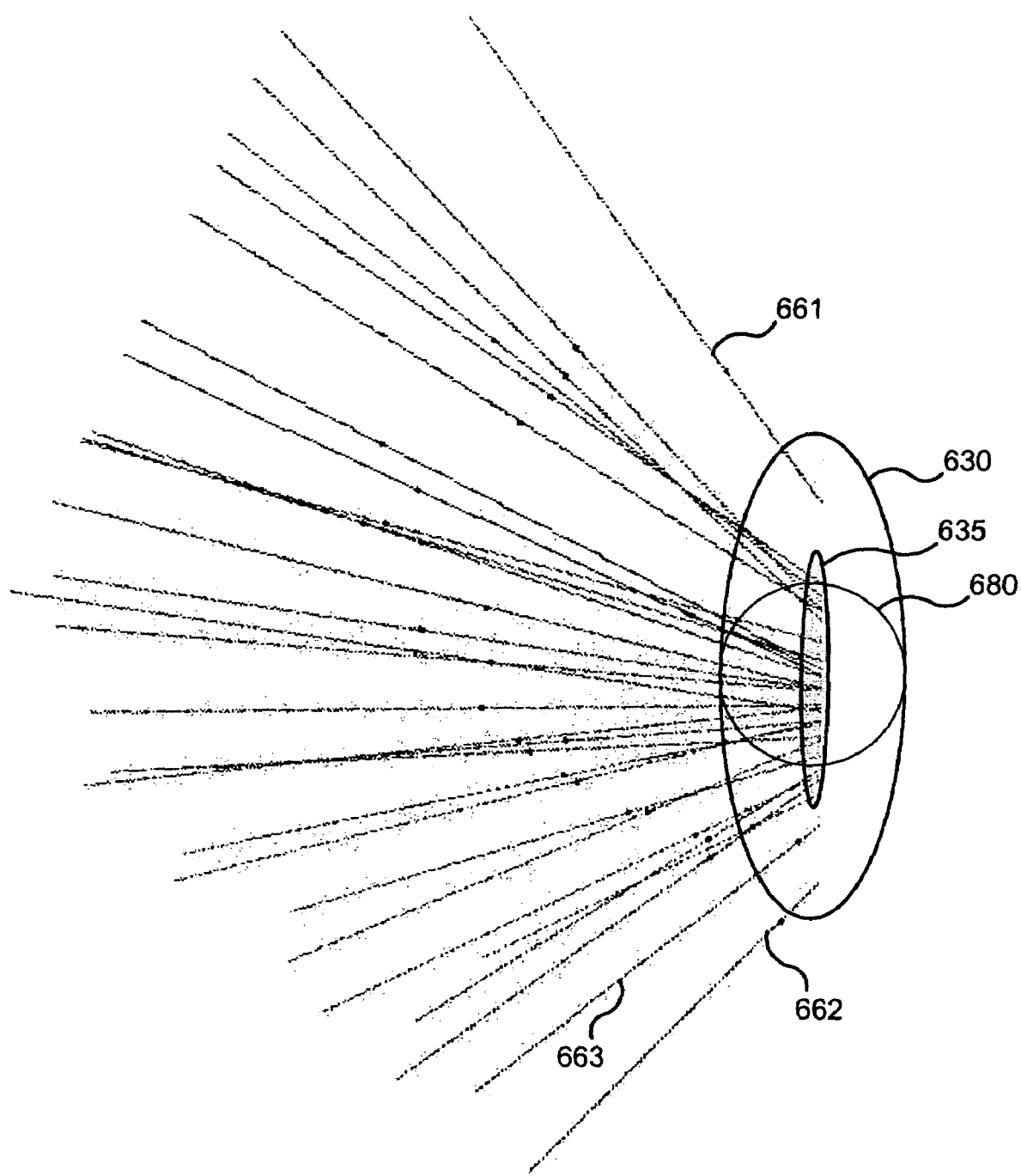
FIG. 6 shows an intra cranial axial view illustrating an exemplary embodiment of a non-isocentric beam profile to treat an elongated target region.

FIG. 6 shows an intra cranial axial view illustrating an exemplary embodiment of a non-isocentric beam profile to treat an elongated target region. In this embodiment, a non-isocentric beam profile is delivered to the elongated target 630. However, the treatment plan may be developed using both forward planning and an inverse planning techniques whereby a forward planning process is used to select only certain beams targeted at the central region 635 of the tumor target 630, and then an inverse planning process is used to weight the selected beams.

In this embodiment, unlike an isocentric form of forward planning, each available beam is not targeted at the same point to form an isocenter. Rather, inverse planning techniques are used to plan a non-isocentric beam profile for the entire target 630. However, similar to forward planning, in this embodiment, the user may specify particular beams (i.e., choose a subset of available beams) from the planned non-isocentric profile that tend to target the central region 635 of the elongated target tumor 630. For example, the user may choose to select all of the illustrated beams (e.g., the chosen subset of the all the illustrated beams) except for beams 661-663 which do not intersect with the central region 635. It should be noted that the process may be one by which the user selects the desired beams and/or de-selects beams that are not desired.

Then, an inverse planning process is used whereby either the user, or the treatment planning module, assigns weights (step 286 of FIG. 2C) to the beams. The treatment planning system then re-calculates the resulting dose distribution. The user may evaluate the resulting dose distribution and manually change his or her selection of beams in an attempt to improve the dose distribution. The treatment planning system may re-calculate yet another resulting dose distribution. This process may be repeated, until the user is satisfied by the resulting dose distribution, as compared to a desired distribution. Circle 680 indicates a collimator size, for the LINAC that produces the beams, to be used in one position Collimator size may be chosen by the user or be chosen automatically by the inverse planning algorithm. A bigger collimator (for example 60 mm) produces a larger beam compared to a smaller collimator (for example 5 mm). For this example, note that the collimator is smaller than the target and therefore encompasses just a portion of that target.

Figure 7:
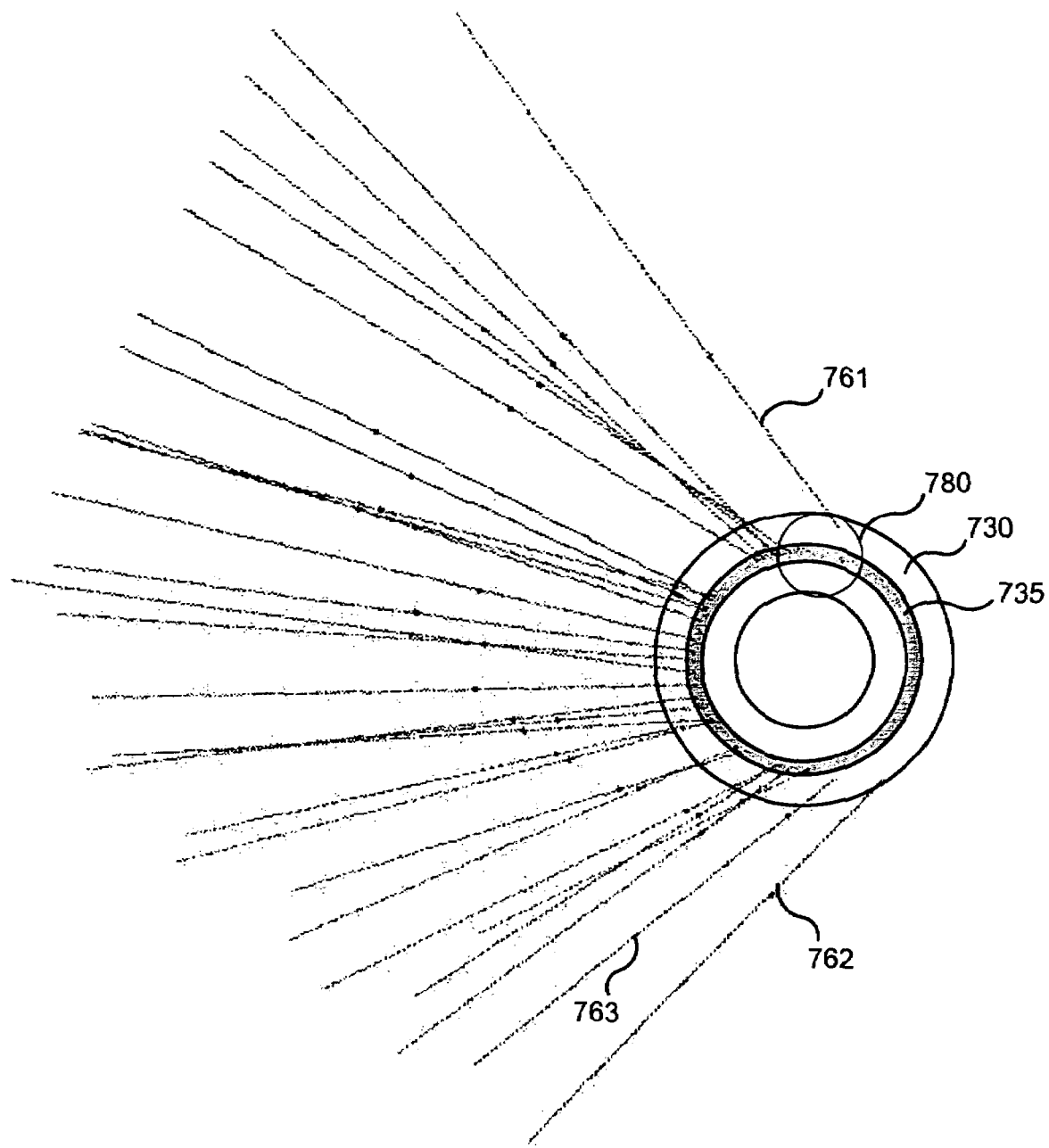
FIG. 7 illustrates another exemplary embodiment of a non-isocentric beam profile to treat a ring shaped target region.

FIG. 7 illustrates another exemplary embodiment of a non-isocentric beam profile to treat a ring shaped target region. In this embodiment, a non-isocentric beam profile is delivered to the ring shaped target 730. Similar to the process discussed above in relation to FIG. 6, a treatment plan may be developed using both forward planning and an inverse planning techniques whereby a forward planning process is used to select only certain beams targeted at the central region 735 of the ring shaped target 730 and then an inverse planning process is used to deliver the selected beams. The user may specify particular beams (i.e., choose a subset of available beams) from a planned non-isocentric profile that tend to target the central region 735 of the ring shaped target 730. For example, the user may choose to select all of the illustrated beams (e.g., the chosen subset of the illustrated beams) except for beams 761-763 which do not intersect with the central region 735. As previously noted, the process may be one by which the user selects the desired beams and/or de-selects beams that are not desired.

Then, an inverse planning process is used whereby either the user, or the treatment planning module, assigns weights (step 286 of FIG. 2C) to the beams. The treatment planning system then re-calculates the resulting dose distribution. As described above, this process may be repeated, until the user is satisfied by the resulting dose distribution, as compared to a desired distribution.

Figure 10:
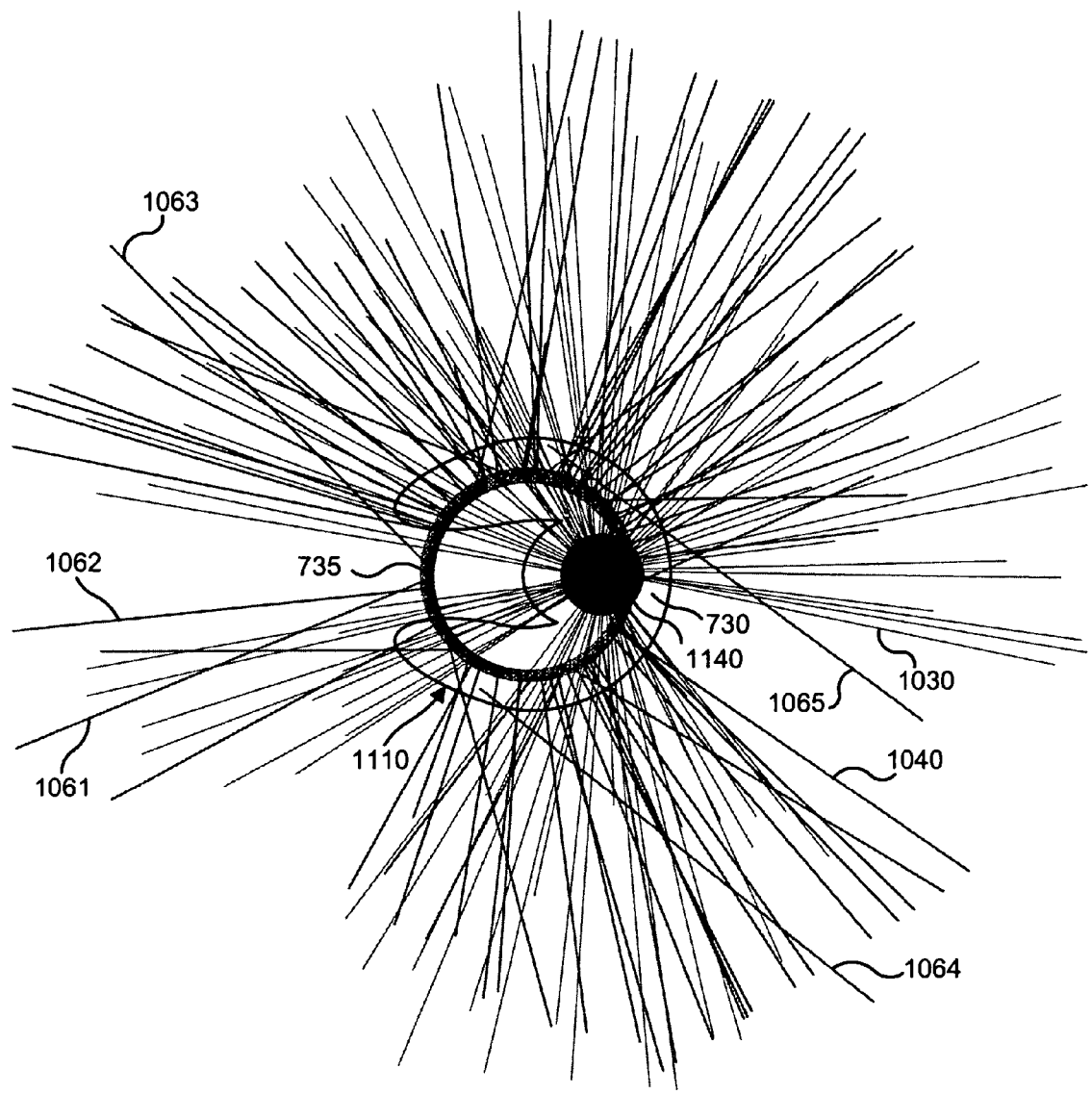
FIG. 10 illustrates one embodiment of a combined isocentric and non-isocentric beam profile to treat an irregular shaped tumor.

FIG. 10 illustrates one embodiment of a combined isocentric and non-isocentric beam profile to treat an irregular shaped tumor. In this embodiment, an isocentric planning process similar to those discussed above in regards to FIG. 1 may be used to target the bulk region 1110 of an irregular shaped tumor 1110. While a mixed planning process similar to that described above in regards to FIG. 7 may be used to target the outer regions of the tumor 1110. More specifically, a non-isocentric beam profile (as exemplified by beam 1064) is delivered to a portion of a ring shaped target 730 of FIG. 10 using a treatment plan developed using both forward planning and inverse planning techniques. A forward planning process is used to select only certain beams targeted at the central region 735 of the ring shaped target 730 that overlap the tumor 1110 and then an inverse planning process is used to weight the selected beams. The user may specify particular beams (i.e., choose a subset of available beams) from a planned non-isocentric profile that tend to target the central region 735 of the ring shaped target 730 or deselect undesired beams that do not tend to target central region 735 (e.g., beams 1064 and 1065) and/or do not target regions of the tumor (e.g., beams 1061-1063). Then, an inverse planning process is used whereby either the user, or the treatment planning module, assigns weights (step 286 of FIG. 2C) to the beams. The treatment planning system then re-calculates the resulting dose distribution. As described above, this process may be repeated, until the user is satisfied by the resulting dose distribution, as compared to a desired distribution.

Figure 4:
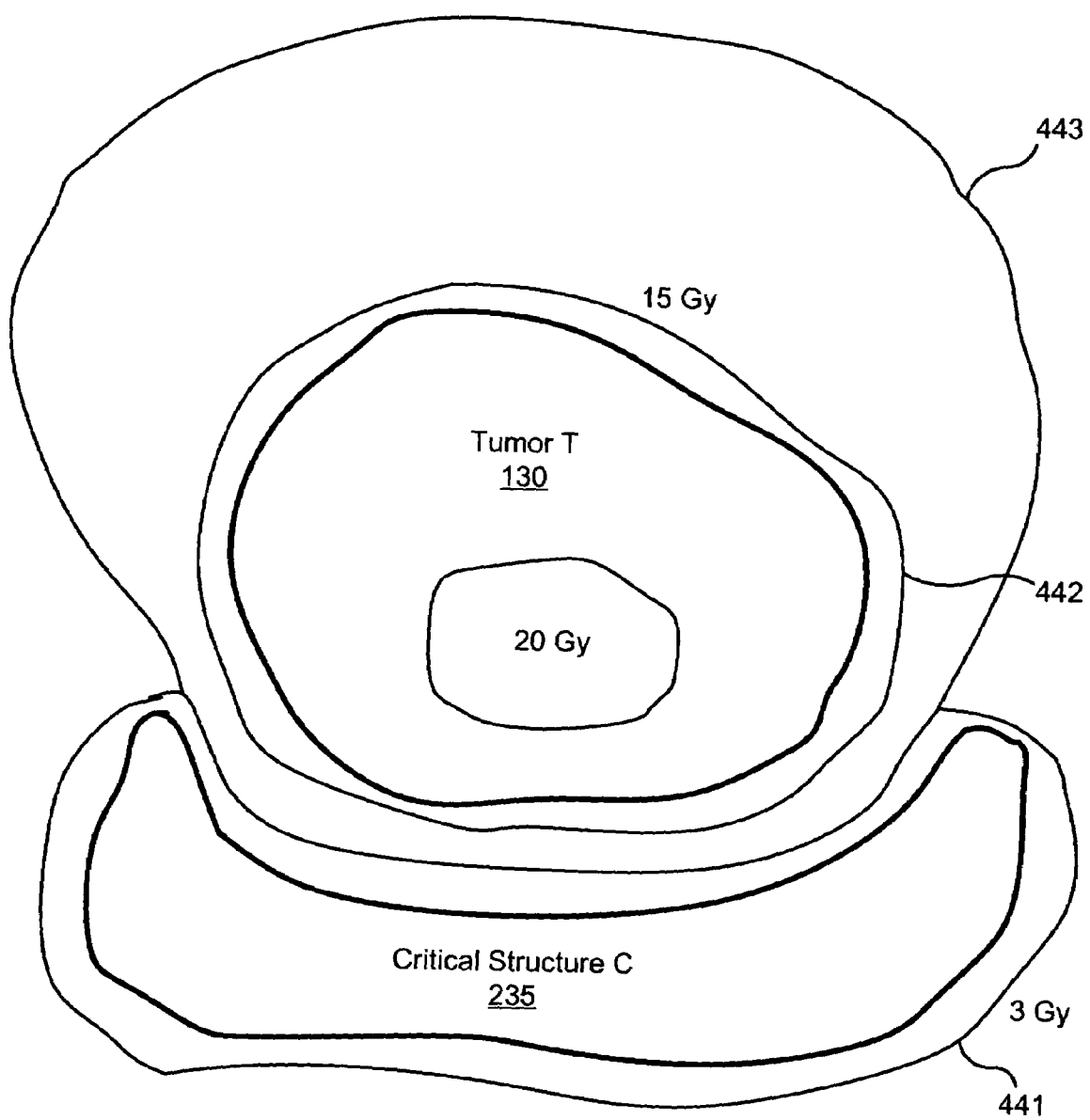
FIG. 4 illustrates a series of isodose curves specified along with a tumor and a critical structure.

FIG. 4 illustrates a series of isodose curves specified along with a tumor and a critical structure. In one embodiment, the treatment planning system may provide an isodose-based inverse planning technique, in which the user can specify isodose contours (e.g., curve 441, 442, 443), as well as acceptable dose ranges for a tumor 130 and critical structure 235. FIG. 4 illustrates exemplary isodose curves 441, 442, 443 corresponding to 3, 15, and 20 Gy values, respectively, that the user specified. The inverse planning problem can now be specified as follows:

Find the plan x with beams that minimizes the objective function J(x) such that $D_i = D_{iprescribed}$ for each pixel on isodose curve i, Isodose based constraints give a user a more direct control on the desired overall dose distribution. Since the user is looking for the optimal overall dose distribution, this method reduces the effect on the results based on the selection of objective function J.

Accordingly, in one embodiment, the inverse planning process utilizes both isodose-based and region-based inverse planning formulations, as follows:

Find the plan x with beams that minimizes the objective function J(x) such that:

$D_i = D_{iprescribed}$ for each pixel on isodose curve i, $D_T(x) < D_{Tmax}$ for each pixel in Tumor T $D_T(x) > D_{Tmin}$ for each pixel in Tumor T
$D_C(x) < D_{Cmax}$ for each pixel in Critical structure C.

The optimization variables x vary, depending on the planning system, and are the monitor units of each of the beams that the machine is capable of generating, which in one embodiment may not be more than 1200 or 1300 beams. Alternatively, another number of beams may be used.

In one embodiment, the treatment planning system may also provide a user with the flexibility to directly modify a topological map of the isodose distribution generated for inverse planning, during use. In such an embodiment, the treatment planning system includes a drawing device interactive with a system display that is responsive to user action, to draw on a display screen contours representative of at least one desired radiation isodose contour and associated radiation value within the image. The treatment planning system may generate isodose contour data representative of the isodose contour lines and associated radiation value. In this embodiment, a processing device within the treatment planning system is responsive to the isodose contour data to determine the beam paths and associated radiation emission points and radiation intensities for affecting a radiation pattern in the anatomical structure characterized by the desired radiation isodose contours.

Figure 8:
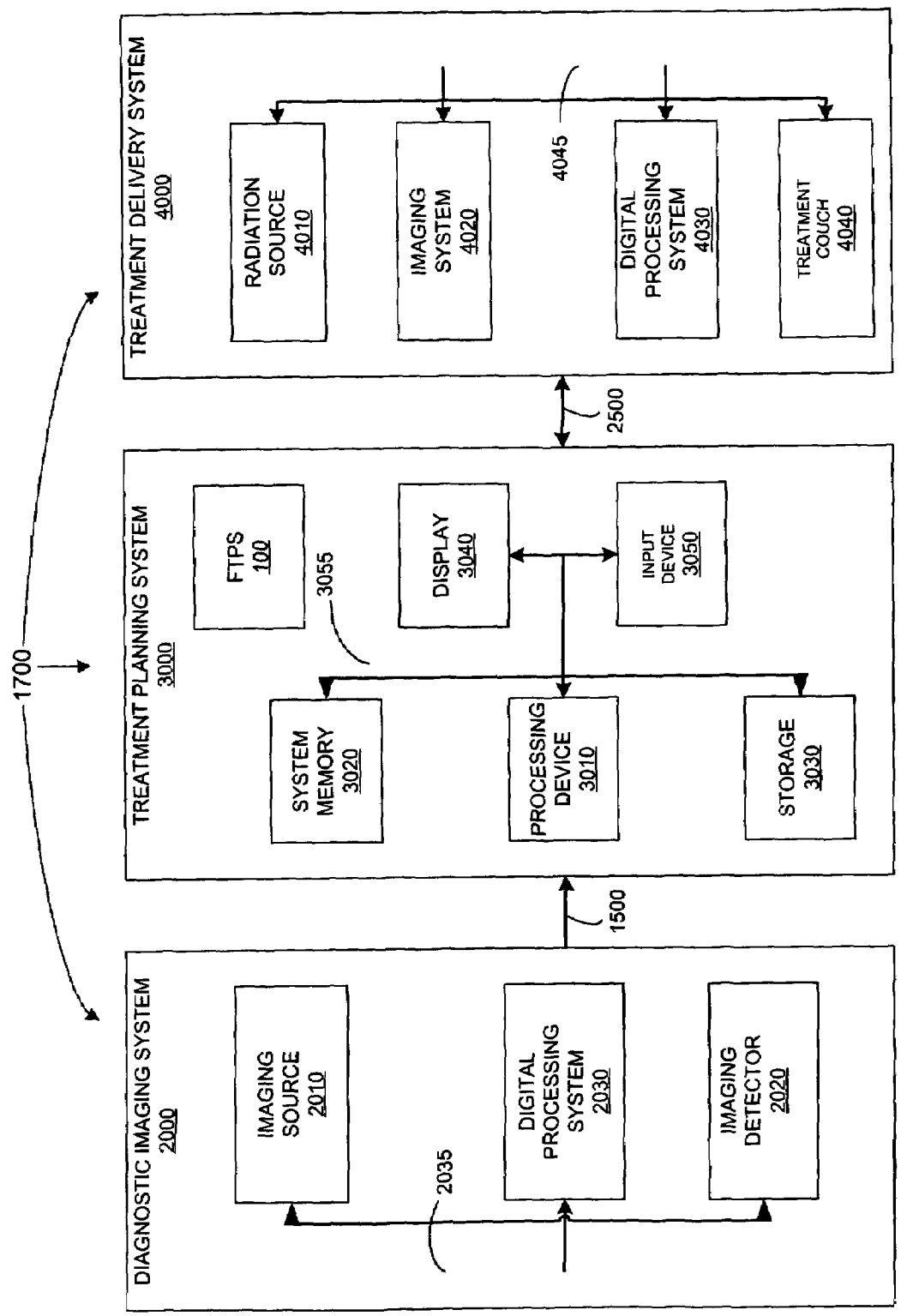
FIG. 8 illustrates one embodiment of systems that may be used to perform radiation treatment in which features of the present invention may be implemented.

FIG. 8 illustrates one embodiment of systems that may be used to perform radiation treatment in which features of the present invention may be implemented. As described below and illustrated in FIG. 17, system 1000 may include a diagnostic imaging system 2000, a treatment planning system 3000, and a treatment delivery system 4000.

Diagnostic imaging system 2000 may be any system capable of producing medical diagnostic images of a volume of interest (VOI) in a patient that may be used for subsequent medical diagnosis, treatment planning and/or treatment delivery. For example, diagnostic imaging system 2000 may be a computed tomography (CT) system, a magnetic resonance imaging (MRI) system, a positron emission tomography (PET) system, an ultrasound system or the like. For ease of discussion, diagnostic imaging system 2000 may be discussed below at times in relation to a CT x-ray imaging modality. However, other imaging modalities such as those above may also be used.

Diagnostic imaging system 2000 includes an imaging source 2010 to generate an imaging beam (e.g., x-rays, ultrasonic waves, radio frequency waves, etc.) and an imaging detector 2020 to detect and receive the beam generated by imaging source 2010, or a secondary beam or emission stimulated by the beam from the imaging source (e.g., in an MRI or PET scan). In one embodiment, diagnostic imaging system 2000 may include two or more diagnostic X-ray sources and two or more corresponding imaging detectors. For example, two x-ray sources may be disposed around a patient to be imaged, fixed at an angular separation from each other (e.g., 90 degrees, 45 degrees, etc.) and aimed through the patient toward (an) imaging detector(s) which may be diametrically opposed to the x-ray sources. A single large imaging detector, or multiple imaging detectors, may also be used that would be illuminated by each x-ray imaging source. Alternatively, other numbers and configurations of imaging sources and imaging detectors may be used.

The imaging source 2010 and the imaging detector 2020 are coupled to a digital processing system 2030 to control the imaging operation and process image data. Diagnostic imaging system 2000 includes a bus or other means 2035 for transferring data and commands among digital processing system 2030, imaging source 2010 and imaging detector 2020. Digital processing system 2030 may include one or more general-purpose processors (e.g., a microprocessor), special purpose processor such as a digital signal processor (DSP) or other type of device such as a controller or field programmable gate array (FPGA). Digital processing system 2030 may also include other components (not shown) such as memory, storage devices, network adapters and the like. Digital processing system 2030 may be configured to generate digital diagnostic images in a standard format, such as the DICOM (Digital Imaging and Communications in Medicine) format, for example. In other embodiments, digital processing system 2030 may generate other standard or non-standard digital image formats. Digital processing system 2030 may transmit diagnostic image files (e.g., the aforementioned DICOM formatted files) to treatment planning system 3000 over a data link 1500, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treatment plan despite the existence of a physical separation between the system user and the patient.

Treatment planning system 3000 includes a processing device 3010 to receive and process image data. Processing device 3010 may represent one or more general-purpose processors (e.g., a microprocessor), special purpose processor such as a digital signal processor (DSP) or other type of device such as a controller or field programmable gate array (FPGA). Processing device 3010 may be configured to execute instructions for performing treatment planning operations discussed herein, for example, automatically generating an envelope of constraint points based on the anatomical shape of a pathological anatomy, and optimizing a current dose isocontour utilizing the envelope of constraint points.

Treatment planning system 3000 may also include system memory 3020 that may include a random access memory (RAM), or other dynamic storage devices, coupled to processing device 3010 by bus 3055, for storing information and instructions to be executed by processing device 3010. System memory 3020 also may be used for storing temporary variables or other intermediate information during execution of instructions by processing device 3010. System memory 3020 may also include a read only memory (ROM) and/or other static storage device coupled to bus 3055 for storing static information and instructions for processing device 3010.

Treatment planning system 3000 may also include storage device 3030, representing one or more storage devices (e.g., a magnetic disk drive or optical disk drive) coupled to bus 3055 for storing information and instructions. Storage device 3030 may be used for storing instructions for performing the treatment planning steps discussed herein, such as the dilution and erosion algorithms.

Processing device 3010 may also be coupled to a display device 3040, such as a cathode ray tube (CRT) or liquid crystal display (LCD), for displaying information (e.g., a two-dimensional or three-dimensional representation of the VOI) to the user. An input device 3050, such as a keyboard, may be coupled to processing device 3010 for communicating information and/or command selections to processing device 3010. One or more other user input devices (e.g., a mouse, a trackball or cursor direction keys) may also be used to communicate directional information, to select commands for processing device 3010 and to control cursor movements on display 3040.

It will be appreciated that treatment planning system 3000 represents only one example of a treatment planning system, which may have many different configurations and architectures, which may include more components or fewer components than treatment planning system 3000 and which may be employed with the present invention. For example, some systems often have multiple buses, such as a peripheral bus, a dedicated cache bus, etc. The treatment planning system 3000 may also include MIRIT (Medical Image Review and Import Tool) to support DICOM import (so images can be fused and targets delineated on different systems and then imported into the treatment planning system for planning and dose calculations), expanded image fusion capabilities that allow the user to treatment plan and view dose distributions on any one of various imaging modalities (e.g., MRI, CT, PET, etc.). Treatment planning systems are known in the art; accordingly, a more detailed discussion is not provided.

Treatment planning system 3000 may share its database (e.g., data stored in storage device 3030) with a treatment delivery system, such as treatment delivery system 4000, so that it may not be necessary to export from the treatment planning system prior to treatment delivery. Treatment planning system 3000 may be linked to treatment delivery system 4000 via a data link 2500, which may be a direct link, a LAN link or a WAN link as discussed above with respect to data link 1500. It should be noted that when data links 1500 and 2500 are implemented as LAN or WAN connections, any of diagnostic imaging system 2000, treatment planning system 3000 and/or treatment delivery system 4000 may be in decentralized locations such that the systems may be physically remote from each other. Alternatively, any of diagnostic imaging system 2000, treatment planning system 3000 and/or treatment delivery system 4000 may be integrated with each other in one or more systems.

Treatment delivery system 4000 includes a therapeutic and/or surgical radiation source 4010 to administer a prescribed radiation dose to a target volume in conformance with a treatment plan. Treatment delivery system 4000 may also include an imaging system 4020 to capture intra-treatment images of a patient volume (including the target volume) for registration or correlation with the diagnostic images described above in order to position the patient with respect to the radiation source. Treatment delivery system 4000 may also include a digital processing system 4030 to control radiation source 4010, imaging system 4020, and a patient support device such as a treatment couch 4040.

Digital processing system 4030 may include one or more general-purpose processors (e.g., a microprocessor), special purpose processor such as a digital signal processor (DSP) or other type of device such as a controller or field programmable gate array (FPGA). Digital processing system 4030 may also include other components (not shown) such as memory, storage devices, network adapters and the like. Digital processing system 4030 may be coupled to radiation source 4010, imaging system 4020 and treatment couch 4040 by a bus 4045 or other type of control and communication interface.

Figure 9:
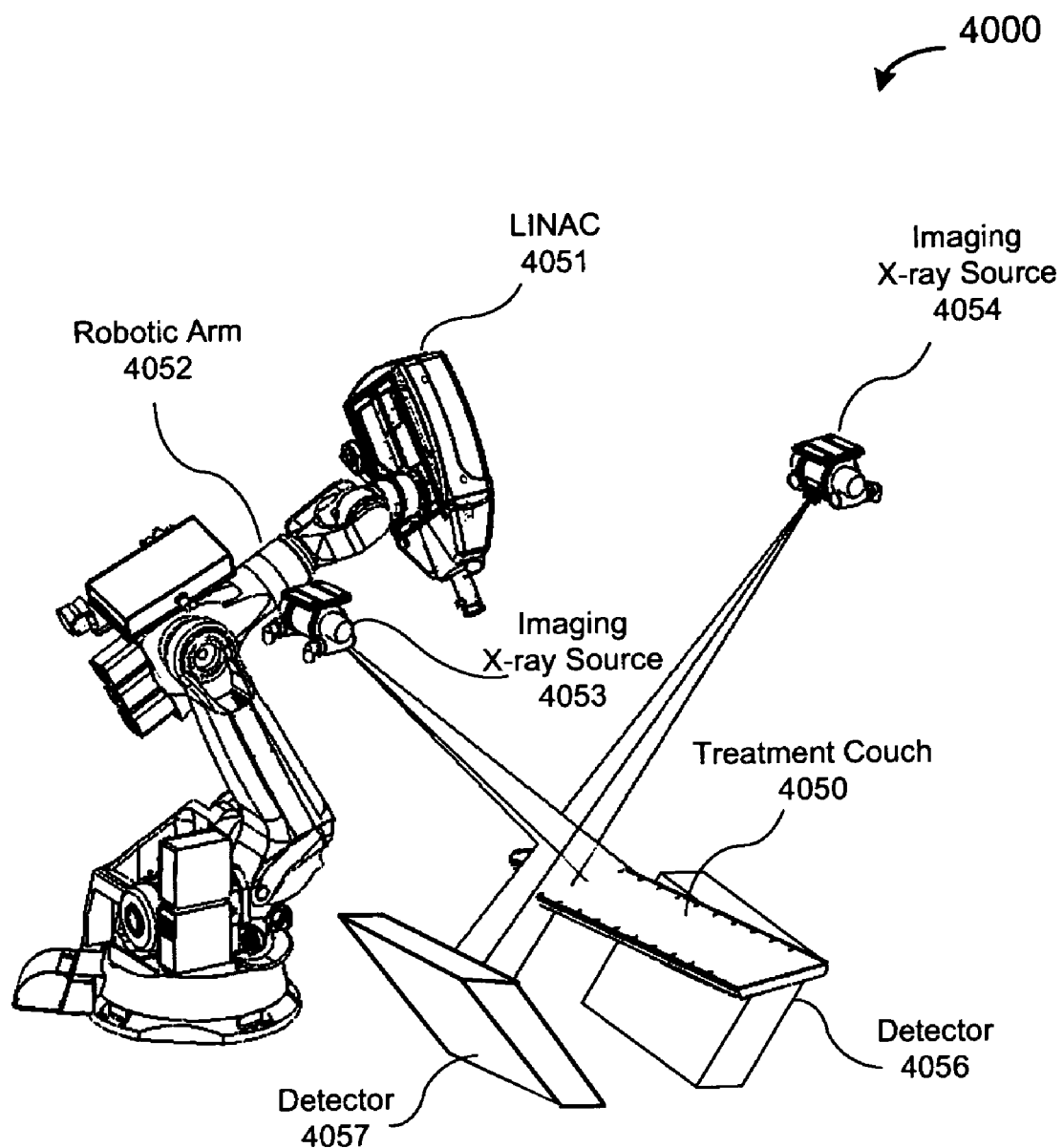
FIG. 9 illustrates one embodiment of an image-guided, robotic-based radiation treatment system.

In one embodiment, as illustrated in FIG. 9, treatment delivery system 4000 may be an image-guided, robotic-based radiation treatment system (e.g., for performing radiosurgery) such as the CyberKnife® system developed by Accuray Incorporated of California. In FIG. 18, radiation source 4010 may be represented by a linear accelerator (LINAC) 4051 mounted on the end of a robotic arm 4052 having multiple (e.g., 5 or more) degrees of freedom in order to position the LINAC 4051 to irradiate a pathological anatomy (target region or volume) with beams delivered from many angles in an operating volume (e.g., a sphere) around the patient. Treatment may involve beam paths with a single isocenter (point of convergence), multiple isocenters, or with a non-isocentric approach (i.e., the beams need only intersect with the pathological target volume and do not necessarily converge on a single point, or isocenter, within the target as illustrated in FIG. 1). Treatment can be delivered in either a single session (mono-fraction) or in a small number of sessions as determined during treatment planning. With treatment delivery system 4000, in one embodiment, radiation beams may be delivered according to the treatment plan without fixing the patient to a rigid, external frame to register the intra-operative position of the target volume with the position of the target volume during the pre-operative treatment planning phase.

In FIG. 9, imaging system 4020 may be represented by X-ray sources 4053 and 4054 and X-ray image detectors (imagers) 4056 and 4057. In one embodiment, for example, two x-ray sources 4053 and 4054 may be nominally aligned to project imaging x-ray beams through a patient from two different angular positions (e.g., separated by 90 degrees, 45 degrees, etc.) and aimed through the patient on treatment couch 4050 toward respective detectors 4056 and 4057. In another embodiment, a single large imager can be used that would be illuminated by each x-ray imaging source. Alternatively, other numbers and configurations of imaging sources and imagers may be used.

Digital processing system 4030 may implement algorithms to register images obtained from imaging system 4020 with pre-operative treatment planning images in order to align the patient on the treatment couch 4050 within the treatment delivery system 4000, and to precisely position the radiation source with respect to the target volume.

The treatment couch 4050 may be coupled to another robotic arm (not illustrated) having multiple (e.g., 5 or more) degrees of freedom. The couch arm may have five rotational degrees of freedom and one substantially vertical, linear degree of freedom. Alternatively, the couch arm may have six rotational degrees of freedom and one substantially vertical, linear degree of freedom or at least four rotational degrees of freedom. The couch arm may be vertically mounted to a column or wall, or horizontally mounted to pedestal, floor, or ceiling. Alternatively, the treatment couch 4050 may be a component of another mechanical mechanism, such as the Axum® treatment couch developed by Accuray, Inc. of California, or be another type of conventional treatment table known to those of ordinary skill in the art.

Alternatively, treatment delivery system 4000 may be another type of treatment delivery system, for example, a gantry based (isocentric) intensity modulated radiotherapy (IMRT) system. In a gantry based system, a radiation source (e.g., a LINAC) is mounted on the gantry in such a way that it rotates in a plane corresponding to an axial slice of the patient. Radiation is then delivered from several positions on the circular plane of rotation. In IMRT, the shape of the radiation beam is defined by a multi-leaf collimator that allows portions of the beam to be blocked, so that the remaining beam incident on the patient has a pre-defined shape. The resulting system generates arbitrarily shaped radiation beams that intersect each other at the isocenter to deliver a dose distribution to the target. In IMRT planning, the optimization algorithm selects subsets of the main beam and determines the amount of time that the patient should be exposed to each subset, so that the prescribed dose constraints are best met.

In other embodiments, yet another type of treatment delivery system 4000 may be used, for example, a stereotactic frame system such as the GammaKnife®, available from Elekta of Sweden. With such a system, the optimization algorithm (also referred to as a sphere packing algorithm) of the treatment plan determines the selection and dose weighting assigned to a group of beams forming isocenters in order to best meet provided dose constraints.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the effectuation of an operation controlled by the TPS, such as the application of a beam (e.g., radiation, acoustic, etc.).

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method, comprising:
   performing forward planning, at least in part, to develop a treatment plan using a first subset of beams of a plurality of beams, wherein performing forward planning comprises selecting a direction and an intensity for each beam in the first subset of beams; and
   performing inverse planning, at least in part to develop the treatment plan.

2. The method of claim 1, wherein inverse planning is performed using a second subset of beams of the plurality of beams.

3. The method of claim 1, wherein the second subset of beams does not include any of the first subset of beams.

4. The method of claim 1, wherein the second subset of beams includes one or more beams from the first subset of beams.

5. The method of claim 2, wherein each of the plurality of beams is characterized by a plurality of parameters comprising a radiation emission point, a distance to a target, an orientation, and a radiation dose weight, and wherein selecting the direction comprises selecting the radiation emission point and the orientation for each beam in the first subset of beams.

6. The method of claim 5, wherein at least one of the plurality of parameters of each beam in the first subset of beams is generated by a user, and wherein at least one of the parameters of the second subset of beams is generated by an inverse treatment planning module.

7. The method of claim 6, wherein the second subset of beams may include one or more beams from the first subset of beams.

8. The method of claim 7, wherein the second subset of beams does not include any of the first subset of beams.

9. The method of claim 1, wherein
   performing forward planning comprises selecting the first subset of beams from among the plurality of beams, wherein each beam in the first subset of beams is based on user generated values representative of a radiation emission point, a target point, and a radiation dose weight; and wherein
   performing inverse planning comprises determining at least one of the radiation emission points, the target point and the radiation dose weight of a second subset of beams.

10. The method of claim 1, wherein selecting the direction comprises selecting an emission point and an orientation for each of the first subset of beams.

11. The method of claim 10, wherein performing forward planning comprises generating a dose distribution.

12. The method of claim 1, wherein performing forward planning further comprises generating a first beam profile with the first subset of beams to target a bulk region of a target, and wherein performing inverse planning comprises generating a second beam profile with the second subset of beams to target a boundary region of the target.

13. The method of claim 12, wherein the first beam profile is an isocentric beam profile and wherein the second beam profile is a non-isocentric beam profile.

14. The method of claim 1, wherein performing forward planning further comprises generating a first beam profile with the first subset of beams to target a higher intensity region of a target, and wherein performing inverse planning comprises generating a second beam profile with the second subset of beams to target a lower intensity region of the target.

15. The method of claim 1, wherein performing inverse planning comprises generating a non-isocentric beam profile with the plurality of beams and wherein performing forward planning comprises choosing the first subset of beams from among the plurality of beams.

16. The method of claim 15, wherein performing inverse planning further comprises:
assigning weights to each of the first subset of beams; and recalculating a resulting dose distribution from the first subset of beams.

17. The method of claim 16 wherein performing inverse planning further comprises changing the chosen first subset of beams.

18. The method of claim 12, wherein the target has a regular shape.

19. The method of claim 12, wherein the target has an irregular shape.

20. The method of claim 1, wherein inverse planning is performed using the first subset of beams.

21. A treatment planning system, comprising a forward treatment planning module integrated with an inverse treatment planning module to develop a same treatment plan, wherein the forward planning module is configured to enable a user to select a direction and an intensity for a first subset of beams of a plurality of beams.

22. The treatment planning system of claim 21, wherein the forward treatment planning module is configured to develop a portion of the treatment plan using forward treatment planning techniques; and wherein
the inverse treatment planning module is coupled with the forward treatment planning module, the inverse treatment planning module is configured to develop another portion of the treatment plan.

23. The treatment planning system of claim 21, wherein the forward planning module is configured to enable the user to select the first subset of beams from among the plurality of beams, wherein each beam in the first subset of beams is based on user generated values representative of a radiation emission point, a target point and a radiation dose weight, and wherein the inverse planning module is configured to determine at least one of the radiation emission points, the target point and the radiation dose weight of a second subset of beams of the plurality of beams.

24. The treatment planning system of claim 21, wherein enabling the user to select the direction comprises enabling the user to select a radiation emission point and an orientation for each of the plurality of radiation beams.

25. The treatment planning system of claim 21, wherein the forward planning module is configured to generating a dose distribution.

26. The treatment planning system of claim 21, wherein the forward treatment planning module is configured to generate a first beam profile with the first subset of beams to target a bulk region of a target, and wherein the inverse treatment planning module is configured to generate a second beam profile with the second subset of beams to target a boundary region of the target.

27. The treatment planning system of claim 26, wherein the first beam profile is an isocentric beam profile and wherein the second beam profile is a non-isocentric beam profile.

28. The treatment planning system of claim 21, wherein the forward treatment planning module is configured to generate a first beam profile with the first subset of beams to target a higher intensity region of a target, and wherein the inverse treatment planning module is configured to generate a second bean profile with the second subset of beams to target a lower intensity region of the target.

29. The treatment planning system of claim 21, wherein the inverse treatment planning module is configured to generate a non-isocentric beam profile with the plurality of beams and wherein the forward treatment planning module is configured to enable choosing of the first subset of beams from among the plurality of beams.

30. The treatment planning system of claim 29, wherein the inverse treatment planning module is further configured to assign weights to each of the first subset of beams and recalculating a resulting dose distribution from the first subset of beams.

31. The treatment planing system of claim 30, wherein the inverse treatment planning module is further configured to enable changing of the chosen first subset of beams.

32. The treatment planning system of claim 26, wherein the target has a regular shape.

33. The treatment planning system of claim 26, wherein the target has an irregular shape.

34. The treatment planning system of claim 21, wherein inverse treatment planning module is configured to develop the treatment plan using the first subset of beams.

35. A treatment planning system, comprising:
means for developing a treatment plan using, at least in part, a forward planning module, wherein the forward planning module is configured to enable a user to select a direction and an intensity for each of a first subset of beams; and
means for developing the treatment plan using, at least in part, an inverse planning module.

36. An article of manufacture, comprising:
a machine-accessible medium including data that, when accessed by a machine, cause the machine to perform operations comprising:
developing, at least in part, a treatment plan based on user inputted forward treatment plan parameters comprising a radiation emission point, a target point and a radiation dose weight for a first subset of beams; and
developing, at least in part, the treatment plan using an inverse planning algorithm.

37. The article of manufacture of claim 36, wherein developing, at least in part, the treatment plan using the inverse planning algorithm comprises determining at least one of the radiation emission point, the target point and the radiation dose weight of a second subset of beams.

38. The article of manufacture of claim 37, wherein the second subset of beams includes one or more beams from the first subset of beams.

39. The article of manufacture of claim 38, wherein the second subset of beams does not include any of the first subset of beams.

40. The article of manufacture of claim 36, wherein developing, at least in part, the treatment plan based on user inputted forward treatment plan parameters comprises generating a dose distribution.

41. The article of manufacture of claim 36, wherein developing, at least in part, the treatment plan based on user inputted forward treatment plan parameters comprises enabling the user to select the first subset of beams from among the plurality of beams, and wherein developing, at least in part, the treatment plan using the inverse planning algorithm comprises determining at least one of the radiation emission points, the target point and the radiation dose weight of a second subset of beams of the plurality of beams.

* * * * *